(12) United States Patent
Grinvald et al.

(10) Patent No.: US 6,478,424 B1
(45) Date of Patent: Nov. 12, 2002

(54) NON-INVASIVE IMAGING OF RETINAL FUNCTION

(75) Inventors: Amiram Grinvald, Rehovot (IL); Darin Nelson, Rehovot (IL)

(73) Assignee: Yeda Research and Development Co., Ltd., Rehovot (IL)

(*) Notice: Subject to any disclaimer, the term of this patent is extended or adjusted under 35 U.S.C. 154(b) by 0 days.

(21) Appl. No.: 09/744,716
(22) PCT Filed: Jul. 29, 1999
(86) PCT No.: PCT/IL99/00418
§ 371 (c)(1), (2), (4) Date: Mar. 21, 2001
(87) PCT Pub. No.: WO00/06015
PCT Pub. Date: Feb. 10, 2000

(30) Foreign Application Priority Data

Jul. 31, 1998 (IL) .................................................. 125614

(51) Int. Cl.[7] .................................................. A61B 3/14
(52) U.S. Cl. ........................ 351/206; 600/473; 600/476
(58) Field of Search ................................. 351/205, 206, 351/211, 213, 221; 600/473, 476, 317, 558

(56) References Cited

U.S. PATENT DOCUMENTS 4,569,354 A * 2/1986 Shapiro et al. ............. 600/476
5,400,791 A * 3/1995 Schlier et al. ............. 600/473
5,485,229 A 1/1996 Hare

FOREIGN PATENT DOCUMENTS

WO    WO92/03086    3/1992

OTHER PUBLICATIONS

"Study of Retinal Dystrophy in RCS Rats: A comparison of Mg–ATP Dependent Light Scattering Activity and ERG b–wave" by Deshpande et al., vol. 32, No. 3, 1992 Vision Research.

"Spectrophotometer for Noninvasive Measurement of Intrinsic Fluoroscence and Reflectance of the Occular Fundus" by Delori, vol. 33, No. 31, Nov. 1994 Applied Optics.

* cited by examiner

Primary Examiner—George Manuel
(74) Attorney, Agent, or Firm—Sughrue Mion, PLLC

(57) ABSTRACT

The invention provides a system for imaging reflectance changes, intrinsic or extrinsic fluorescence changes of a retina (6) due to retinal function, including an imaging illuminator (14) for illumination of the retina (6); a retina-stimulating illuminator (2) for inducing a functional response; an imaging device (20) receiving light from the retina (6) via retinal imaging optics (12); image acquisition means (26) for digitizing and storing images received from the imaging device (20), and a computer (28) for controlling the operation of the system and for processing the stored images to reveal a differential functional signal corresponding to the retina's function.

11 Claims, 1 Drawing Sheet

NON-INVASIVE IMAGING OF RETINAL FUNCTION

FIELD OF THE INVENTION

The present invention relates to a system and method for non-invasive imaging of retinal function.

BACKGROUND OF THE INVENTION

In some degenerative retinal diseases, retinal function may be altered even before changes in the retinal tissue occur which are detectable by current, non-functional, diagnostic imaging techniques. In glaucoma, for example, up to 50% of the retinal axons may degenerate before symptoms of pathology or reduced visual acuity are noticed, even by the patient. Due in part to limitations in current diagnostic technology, it is estimated that more than 3,000,000 patients in the U.S. alone are currently undiagnosed victims of treatable eyesight impairment.

Common current ophthalmic diagnostic imaging techniques such as retinal photography, fluorescence angiography, as described, e.g. in WO 92/03086. and retinal tomography, do not directly reveal the state of the retina's function. Retinal photography detects abnormalities in the static coloration of the retina, caused, for example, by hemorrhages, hard yellow exudates, "silver" or "copper" blood vessel opacification, "cotton wool" spots, and blanching of the retina due to retinal edema or anoxia. These correlate with functional deficits, but do not reveal the functional integrity of the retina per se, and may only become obvious some time after pathology has established itself. Similarly, fluorescence angiography, which relies on the pattern of fluorescent labeling of the retina's microvascular network by injected probes such as fluorescein and indocyanine green, provides only indirect information about retinal function. What it does directly reveal are flaws in the retinal vasculature, correlated with, but often subsequent to, certain functional deficits. Finally, retinal tomography can reveal anatomical changes due to reduced numbers of retinal axons, but again, this technique is insensitive to the functional integrity of the retina itself.

The present invention, however, may be used to directly measure the functional integrity of the retina. It is intended to detect electrical activity-dependent changes in the optical properties of the retina, either non-invasively, or after retinal labeling by a specially designed fluorescent probe. These activity-dependent changes are directly related to local retinal responsiveness to visible light. The present invention measures retinal function in one of two modes: an intrinsic signal mode, and a fluorescence signal mode.

The intrinsic signal mode relies on any one of a number of functional optical signals resulting from the retina's native properties. Upon illumination, the functioning retina undergoes changes in its reflectance which are due to alterations in many physiological parameters, including, but not limited to, blood flow, blood oxygenation, light scattering from the retinal axons, light scattering and/or pigment bleaching from the retinal pigmented epithelium, and rod or cone photopigment bleaching. The retina itself thus provides a rich source of optically measurable functional signals, occurring at many different wavelengths and with many different time courses.

When the method according to the present invention is operated in the fluorescence signal mode, the retina of interest may first be labeled with a fluorescent voltage-sensitive probe. Such a probe is a compound which binds to the membranes of retinal neurons and alters its fluorescent properties (emitting more or less light, or shifting its spectral properties, under constant illumination), depending on the electrical field across the membrane of a neuron within which it is bound. Because transmembrane electrical fields are altered when neurons are active, light measurements using such a fluorescent voltage-sensitive probe provide a means for directly assaying retinal activity. Alternatively, a fluorescent signal may be measured by choosing excitation and emission wavelengths appropriate to an intrinsic fluorescent chromophor, such as NADH.

The magnitude of either type of functional optical signal is influenced by the optical properties of the resting retina. Light must pass through any unusually opaque or light-scattering tissue which interposes itself between the active retinal tissue and the illuminator or detector. This modulates the functional signal in a way which may also reveal static abnormalities in the retina's optical properties.

The differences between the reflectance or fluorescence images taken from the resting retina and from the active retina may be encoded as a differential image, in which differences in brightness are due entirely to functional activity, as filtered though any optically manifested retinal abnormalities. Both types of information are of clinical relevance.

The functional changes in reflectance/fluorescence which the present invention measures may be quite small, often no more than 0.1% of the total light received by the imaging device. Small changes in reflectance are not obvious when they occur against a high background level of reflected or fluorescent light, and therefore functional optical imaging has not been previously used to reveal ophthalmic diagnostic information.

A device designed to use functional changes in retinal reflectance (measured point by point, not in image format) to reveal the retina's health is disclosed in U.S. Pat. No. 5,485,229. This prior art invention exclusively uses the previously observed phenomenon of light-scattering changes which occur in active axons, in this case, in the retinal nerve fiber layer. The present invention, however, differs from and improves on this prior art device in several ways. One important improvement over the prior art is in the adaptability of this invention to recording and evaluating multiple types of functional signals, at multiple wavelengths, in opposition to the prior art, which is restricted to one signal type and imaging wavelength. A second point of difference is that the present invention simultaneously images hundreds of thousands to millions of retinal points, improving on the single point resolution of the prior art. A third key difference is in the present invention's application of differential image analysis to a functional retinal signal.

The differential image analysis for revealing a functional signal according to the present invention is novel for use in clinical imaging of the retina, in that it selectively emphasizes metabolically induced variations in reflectance or probe fluorescence, over time, across the retinal surface by removing the stable portion of the image from consideration. A prior art method which relies on the temporal pattern of blood-borne inflow of contrast agents to the retina is described in U.S. Pat. No. 5,150,292, which shares some aspects of the image analysis technique outlined here. However, the method of said patent cannot reveal functional retinal signals, as the present method is especially designed to do.

SUMMARY OF THE INVENTION

In accordance with the present invention, there is therefore provided a system for imaging reflectance changes, intrinsic or extrinsic fluorescence changes of a retina due to normal retinal function, comprising an imaging illuminator for illumination of the retina; a retina-stimulating illuminator for inducing an optically detectable functional response signal; an imaging device receiving light from the retina via retinal imaging optics; image acquisition means for digitizing and storing images received from said imaging device, and computer means for controlling the operation of the system and for processing said stored images to reveal a differential optically detectable functional response signal corresponding to the retina's function.

The invention further provides a method for imaging reflectance changes, intrinsic or extrinsic fluorescence changes of a retina due to normal retinal function, comprising the steps of illuminating a retina with light from a stable light source; imaging and recording the retina's image as illuminated to form a baseline image; illuminating the retina with light having wavelengths appropriate for inducing an optically detectable functional response signal; imaging and recording the retina's image after or during the induction of said functional response signal; illuminating the retina with light having wavelengths appropriate for measuring said signal; performing a differential analysis of said baseline and response images, whereby a differential optically detectable functional response signal corresponding to the retina's normal function is revealed.

BRIEF DESCRIPTION OF THE DRAWING

The invention will now be described in connection with certain preferred embodiments with reference to the following illustrative FIGURE, so that it may be more fully understood.

With specific reference now to the FIGURE in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawing making apparent to those skilled in the art how the several forms of the invention may be embodied in practice.

In the drawing:

FIG. 1 is a block diagram of a preferred embodiment of the apparatus for non-invasive imaging of retinal function according to the present invention.

DETAILED DESCRIPTION OF PREFERRED EMBODIMENTS

Figure 1:
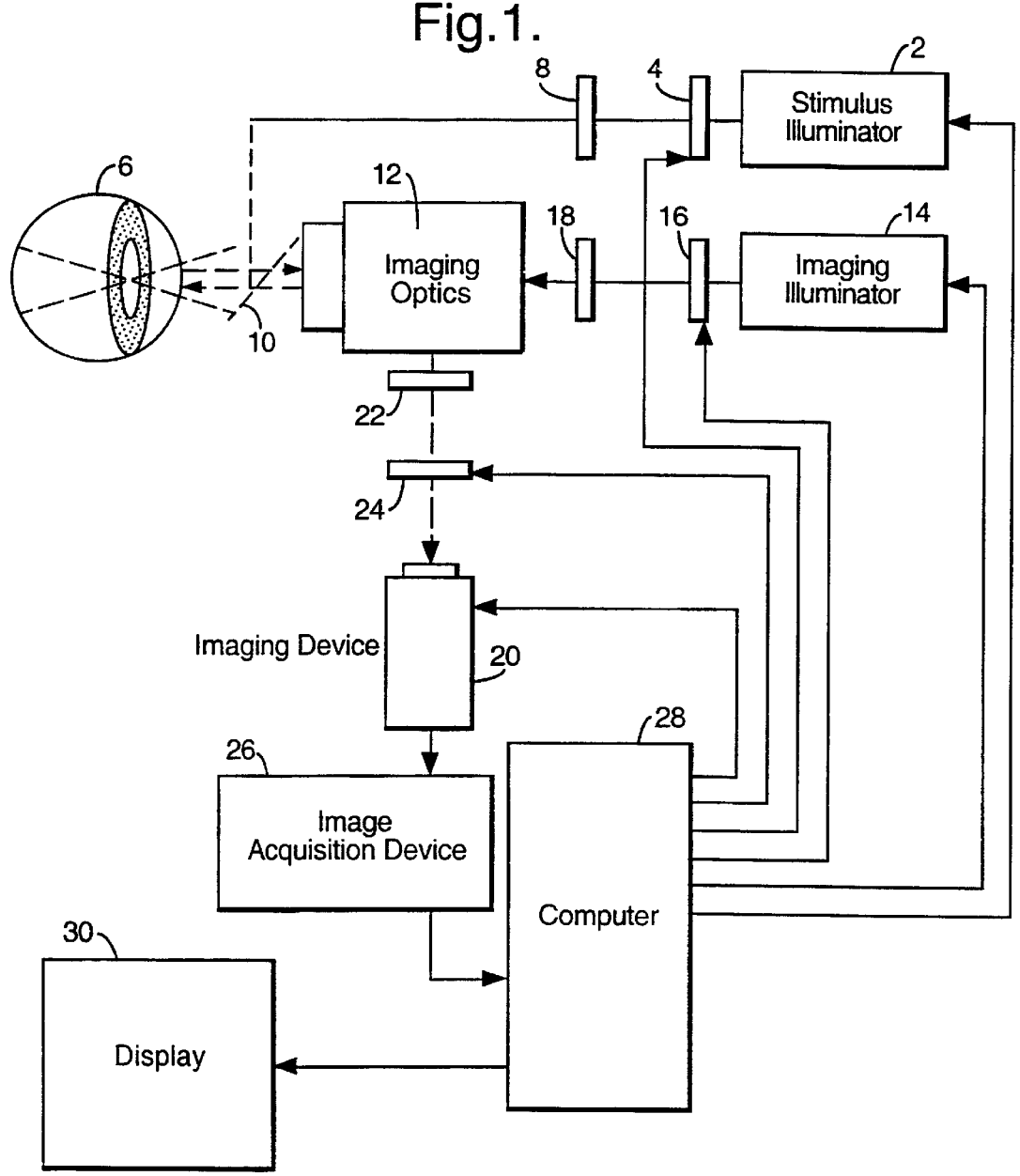

There is seen in FIG. 1 a stimulus illuminator 2, which may be constituted by a computer monitor or any other image display device which controllably displays a visible target. A shutter 4 may also be disposed in the line of sight between the illuminator 2 and the retina 6 of a patient's eye. The display of the illuminator 2 is controlled with respect to duration, timing, wavelength, pattern and intensity. To control more precisely for light wavelength, a light wavelength filter 8 may be placed between the stimulus image and the eye. The image is brought onto the retina 6 by means of a partially reflective mirror 10 interposed between the eye and the (ophthalmic) imaging optics 12. Alternatively, the stimulus illumination may be brought to the retina 6 by the imaging optics 12 themselves. Clearly, other stimulus illumination means may produce substantially the same type of visual stimulation required for functional retinal imaging, including those which use an imaging illuminator 14 as a full-field retinal stimulator, as well as for illuminating for image acquisition.

The imaging illuminator 14 may be a stabilized flash lamp, or may provide illumination from a steady light source (e.g., an incandescent halogen bulb or a stabilized arc lamp), with the incidence of light on the retina 6 controlled by a fast, computer-controllable shutter 16. Stable illumination is important to obtaining good functional signals when imaging biological systems, as the small signal may otherwise be lost due to instabilities in the intensity of the light source itself.

The imaging illumination light may be filtered by filter 18 so as to be of any desired wavelength, or combination of wavelengths, detectable by the imaging device 20, or, in the case of fluorescence measurements, of a wavelength suitable for exciting the voltage-sensitive fluorescent probe being used. For applications in which multiple different wavelengths of illumination may need to be selected over time, a computer-controlled monochromometer or filter wheel can be used in place of fixed wavelength filter 18. In all cases, the timing of the illumination may be subject to computerized control.

It may also be necessary to introduce a filter 22 for filtering the light exiting the retina 6, as well as the light which is used to illuminate or stimulate it. There are at least two situations where this is important. In intrinsic signal mode, in applications where the retina is simultaneously stimulated at one wavelength and imaged at another, it is desirable to place a filter 22 just in front of the imaging device 20, which filter removes reflected light due to the stimulus, while allowing the imaging wavelength to pass. In fluorescence signal mode, post-retinal filtering is required, so that light at the emission wavelength is passed to the imaging device 20, while reflected light at the excitation wavelength is removed.

The adaptability of the present invention to recording and evaluating multiple signal types, at multiple wavelengths, is an improvement over the prior art system, which confines itself to the use of a polarized laser light-scattering signal from axons, which is a rapid signal (on the order of milliseconds). Because the system of the present invention does not rely on an intrinsically monochromatic light source for imaging, it is considerably more flexible than that of the prior art. It can measure the axon scattering signal, as well as many others. For example, by choosing imaging wavelengths within the range of the eye's photopigments (which bleach during retinal activation), disease-related changes in the optical properties of the eye across the whole of the visible spectrum may be revealed. In fluorescence mode, the filters controlling the wavelengths for illuminating and imaging the retina are chosen to be appropriate for the voltage-sensitive probe being used.

Of particular novelty is a new type of retinal intrinsic signal. For the first time, and by using the present invention, a signal which develops over several seconds has been detected, manifesting a gradual increase in the retina's reflectance measured with infrared light at 750 nm, upon exposing the retina to visible light at 540 nm.

This signal exhibits several characteristics which have not been previously observed, and thus is demonstrably distinct from retinal hemodynamic signals, light scattering signals, and signals due to retinal photopigment bleaching. The retina's visual pigments are transparent at infrared wavelengths, and the signal develops after, not during, a brief illuminating stimulus; thus, the signal is not due to bleaching of a photopigment. It is also much slower than, and has an opposite polarity to, the light scattering signal used in the prior art. It differs from a light scattering signal also in that it is wavelength-specific (not seen at wavelengths above 780 nm). Finally, this novel signal is not due to hemodynamic changes, because it exhibits an increase in reflectance and not a decrease, as is true for the signals originating from the retinal microvascular system.

Because it does not rely on the secondary regulation of blood flow through a relatively coarse-threaded bed of capillaries, but instead is directly due to the metabolic activity of cellular elements in the retina, this signal is of higher spatial resolution than previously described hemodynamic signals. Similarly, it is also a more spatially precise signal than the prior art's light-scattering signal, which is distributed along the length of the activated axons and is not confined to the loci of active neuronal cell bodies in the region of photic stimulation. A further advantage of this signal is that it is measurable with a two-dimensional imager, improving on the point-by-point measurements to which the prior art is confined.

The illuminating light is focused on retina 6, and light emitted/reflected from the retina is focused on the imaging device 20, using an optical apparatus standard for imaging the retina 6, which may be constituted by, but is not limited to, either an ophthalmoscope or a fundus camera, with means for attaching thereto an imaging device.

The imaging device 20 may be a high bit-depth (10 or more bits per pixel), digital CCD camera (e.g., a Dalsa CA-D7-102/T) or other high bit-depth, high-resolution imaging device (e.g., a video signal-producing CCD camera attached to an Optical Imaging Imager 2001 differential video amplifier) placed at the imaging plane of imaging optics 12. The imaging device 20 is shuttered by a shutter 24 under computer control. Shutter 24 may be a mechanical or electronic shuttering device, as appropriate. A digital image acquisition device 26 (e.g., a frame grabber such as a Matrox Pulsar) is provided for transferring the image signal from device 20 to the memory of a digital computer 28 for storage and analysis.

The relative timing of the retinal stimulus and the acquisition of images is controlled by equipping computer 28 with a timing I/O interface board, or indirectly from the computer via other appropriate timing hardware. Data acquisition parameters are established by the operator through a user interface provided by computer software. Acquired retinal images are stored by the computer. Analysis of the retinal images is also performed by computer software. Results, in image form, can also be displayed on the computer's monitor or display 30 and printed or otherwise made available for examination.

When the system according to the invention is to be used in fluorescence signal mode, the retina of interest must first be labeled (by injection or other means) with an appropriate voltage-sensitive probe, unless an intrinsic fluorophore is to be used. Voltage-sensitive probes for neural imaging have been described in the prior art, though not their application to diagnosis of retinal dysfunction.

Using a computerized interface, the user selects the stimulus target to be displayed by the stimulus illuminator 2, and, in the more general instance, the wavelength to be output by the imaging illuminator 14. Timing parameters are also selected, which are used by the computer to control the opening and closing of the various shutters 4, 16, 24.

Any of several different illumination timing and wavelength parameters may be chosen. In intrinsic signal mode, these depend on the wavelengths to which the functional signal of interest is sensitive, the wavelength at which the functional signal is best revealed, and the speed with which the signal develops. In fluorescence signal mode, the choice of light-filtering parameters will depend on the absorption and emission characteristics of the intrinsic fluorophore (e.g., NADH) or the voltage-sensitive probe being used. The following are examples of the present invention's uses, without limiting their scope:

1) In fluorescence mode, the stimulus illumination may be a brief flash of a visible target, occurring after the capture of a baseline image of the retina illuminated at the excitation wavelength of the dye, and before one or a series of subsequent images taken to record the functional or voltage signal as it develops.

2) For a very fast light-scattering signal, stimulus and imaging illumination may be short (a few milliseconds) and simultaneous, using white light to stimulate, and near infra-red to infra-red light to image.

3) Photopigment bleaching may similarly be monitored with simultaneous stimulus and imaging illumination (at the same wavelength, or different wavelengths), though over longer periods of time, from hundreds of milliseconds to seconds.

4) A more slowly developing, secondary metabolic signal has been detected with the present invention, apparently for the first time, by first imaging the retina using infra-red light in the 750 nm range, then briefly (100 msec) illuminating it with visible light (e.g., 540 nm), while continuing to record the reflectance of the retina at 750 nm over the next 3–5 seconds.

Upon the onset of stimulation, the stimulus shutter 4 opens and light passes through the illumination-combining optics, e.g., mirror 10, allowing the stimulus and imaging illumination to use the same light path, or enter directly into the imaging optics 12 themselves. Upon the onset of imaging illumination, which may be before, simultaneous with, after, or interleaved with, the onset of stimulus illumination, the illumination shutter 16 opens, and also sends light through the imaging optics 12 and the illumination combining optics or mirror 10.

The combined stimulus and imaging illumination light beams are focused onto the retina 6 of the patient's eye. Light reflected or fluorescing from the eye is recaptured by the retinal imaging optics or mirror 10 and focused onto the imaging plane of a high resolution, two-dimensional imaging device such as a CCD camera, constituting the imaging device 20. A post-illumination filter 22 may be interposed between the retina and the imaging device 20 to filter out the stimulus or excitation wavelengths, when appropriate.

Image information is transmitted from imaging device 20 to the computer 28 via image acquisition device 26, which converts the camera signal to a digital form, if necessary, and controls placing this digital data into the computer's memory. The timing of the acquisition of images by the imaging device 20 is also controlled from the computer 28 on the basis of user-determined parameters. At the computer 28, image data may also be stored on a disk or other long-term digital storage medium.

Analysis of the images may proceed by different routes, differing from one another in certain details. Depending on acquisition parameters, one or several images are designated as baseline images, showing the reflectance/fluorescence of the retina at the imaging wavelengths before, or shortly after, the onset of stimulus illumination. When more than one baseline image is acquired, these may be averaged together to produce a single-condition blank image, in which camera and other noise has been reduced relative to the overall illumination signal. Images from multiple image acquisition episodes may also be averaged.

Other images acquired during or after stimulating retinal illumination are designated response images. Because of the small size of the functional signal, these response images look little different from the baseline images upon cursory examination. However, subsequent analysis reveals the small functional signal they contain. A single-condition response image is obtained from one response image, or, more typically, by averaging together several individual response images taken under the same set of wavelength and timing parameters. These images may be from within one recording episode, or may be combined from multiple recording episodes.

Differential analysis now proceeds by one of two preferred methods. Either the single-condition blank image is subtracted from the single-condition response image, or the single-condition response image is divided by the single-condition blank image. Either of these mathematical operations, or one of others which may be trivially related, removes the unchanging background of the retinal reflectance/fluorescence image, leaving behind the functional response of the retina to visual stimulation. The resulting image is called the differential image, as it selectively reveals differences between two other images.

A differential image need not only be obtained from a single-condition response image and a single-condition blank image. Other, related analytical operations may also reveal relevant functional differences. For example, two single-condition response images may be made under different conditions of illumination, and themselves used to create a differential image. This reveals portions of the retina's functional response specific to the illumination conditions used, rather than due to illumination of the retina per se. This is a method by which the effect of the imaging illumination can be factored out from that of the stimulus illumination proper.

The following example applies this analysis step to a specific case, not intended to be limiting of the uses of the present invention. The present invention may be set to illuminate the retina with infra-red illumination (which, being invisible, does not itself evoke functional changes) while acquiring one image before exposure to the stimulating visible light, and another afterward. Changes occurring between the two images, due to the retina's increased metabolic activity in response to photic activation by visible light (resulting from changes in electrical activity or photopigments bleaching), are revealed by subtracting/dividing one image from/by the other. In the resulting differential image, the unchanging background has been removed. Instead, areas undergoing no functional changes in reflectance are featureless, while others become relatively darker or lighter, depending on the sign of the functional signal.

Background removal reduces the dynamic range of the differential image, so that it can now be rescaled (amplified) to make the previously invisible functional signal visible. An abnormal 50% change in a 0.1% functional signal in a retinal region is easily detectable by this method, while going unnoticed by non-differential imaging techniques.

It should be noted that the divisive analysis procedure has the advantage of normalizing the functional signal according to the intensity of the background reflectance of the retina; thus, the resulting image shows the same intensities for regions which undergo the same percentage of functional change in reflectance, rather than the same absolute amplitude of functional change in light reflected. This internal normalization helps to avoid errors in interpretation of the functional signal which may be caused by uneven illumination of the retina, rather than abnormalities in the retina itself. Alternatively, subtractive differential imaging may sometimes be preferred, precisely because it is sensitive to uneven illumination or reflectance, as may also occur due to (clinically important) optical irregularities on the retinal surface.

Finally, the image values of the divided or subtracted differential image are re-scaled and displayed so that the intensity values of the image extend throughout the dynamic range of the display device (which may be a monitor, printer, or other image-producing apparatus). The values of the differential image may be displayed as a pseudo-color image or as a gray-scale image. Obviously, the differential image may be subject to various standard forms of filtering, binning, etc. to clarify the image, and may also be subject to further analysis to extract clinically relevant parameters.

It will be evident to those skilled in the art that the invention is not limited to the details of the foregoing illustrated embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A system for imaging reflectance changes, intrinsic or extrinsic fluorescence changes of a retina due to normal stimulated retinal function, comprising:

an imaging illuminator for illumination of the retina;

a retina-stimulating illuminator for inducing an optically detectable functional response signal;

an imaging device receiving light from the retina via retinal imaging optics;

image acquisition means for digitizing and storing images received from said imaging device, and computer means for controlling the operation of the system and for processing said stored images to reveal a differential optically detectable functional response signal corresponding to the retina's function;

characterized in that:

said imaging illuminator includes means for illuminating at least a major portion of the retina during at least one selected period of time by selected wavelengths of visible and/or infra-red light;

said illuminator transmits visible light onto said major portion of the retina and said computer means commences operation of the imaging illuminator prior to activation of the retina-stimulating illuminator for a selected period of time, to enable recording of at least two images representing, by their differences, functional changes in the retina due to its illumination by visible light.

2. The system as claimed in claim 1, further comprising a filter disposed in the light path between said stimulus illuminator and said retina.

3. The system as claimed in claim 1, further comprising illumination-combining optics for causing the retina stimulus illumination and the imaging illumination to impinge upon the retina through a partially common light path while preventing light originating at the stimulus illuminator from impinging on said imaging device.

4. The system as claimed in claim 1 fixer comprising a display connected to the output of said computer means.

5. The system as claimed in claim 1, wherein each of said stimulus illuminator and/or said imaging illuminator is provided with a shutter for effecting a controlled illumination of the retina.

6. A method for imaging reflectance changes, intrinsic or extrinsic fluorescence changes of a retina due to normal stimulated retinal function, characterized by the steps of illuminating at least a major portion of a retina with selected wavelengths of visible and/or infra-red light from a stable light source;

imaging and recording the retina's image as illuminated to form a baseline image;

illuminating said portion of the retina with light having wavelengths appropriate for inducing an optically detectable functional response signal;

imaging and recording the retina's image after or during the induction of said functional response signal;

performing a differential analysis of said baseline and response images, whereby a differential optically detectable functional response signal corresponding to the retina's normal function is revealed.

7. The method as claimed in claim 6, further comprising:

acquiring a plurality of baseline images, and averaging at least some of said plurality of images, to form a single-condition blank image.

8. The method as claimed in claim 7, wherein said single-condition blank image and said single-condition response image are subjected to differential analysis to produce a differential image.

9. The method as claimed in claim 6, comprising:

acquiring a plurality of response images, and averaging at least some of said plurality of images, to form a single-condition response image.

10. The method as claimed in claim 6, further comprising the step of labeling said retina with a fluorescent compound serving as a voltage-sensitive probe.

11. The method as claimed in claim 10, comprising the step of illuminating said retina by visible and/or infa-red wavelengths appropriate for recording reflectance changes or intrinsic or extrinsic fluorescence changes in the retina.

* * * * *